United States Patent [19]

Rochat et al.

[11] Patent Number: 4,579,949

[45] Date of Patent: Apr. 1, 1986

[54] PREPARATION OF PYRROLO[3,4-C]PYRROLES

[75] Inventors: Alain C. Rochat, Basel, Switzerland; Luigi Cassar, Bologna, Italy; Abul Iqbal, Ettingen, Switzerland

[73] Assignee: Ciba-Geigy Corporation, Ardsley, N.Y.

[21] Appl. No.: 493,533

[22] Filed: May 11, 1983

[30] Foreign Application Priority Data

May 17, 1982 [CH] Switzerland ................ 3054/82
Sep. 15, 1982 [CH] Switzerland ................ 5468/82

[51] Int. Cl.⁴ .................................... C07D 487/04
[52] U.S. Cl. ........................... 546/167; 546/256; 546/272; 548/453; 524/104
[58] Field of Search ............ 548/453; 546/167, 256, 546/272

[56] References Cited

U.S. PATENT DOCUMENTS 4,415,685 11/1983 Iqbal et al.

OTHER PUBLICATIONS

Hollins Synthesis of Nitrogen Heterocyclic Ring Compounds, p. 52, Benn, London (1924).
D. G. Farnum et al., Tetrahedron Letters, 29, 2549 (1974).

Primary Examiner—Glennon H. Hollrah
Assistant Examiner—D. B. Springer
Attorney, Agent, or Firm—Luther A. R. Hall

[57] ABSTRACT

A process for the preparation of 1,4-diketopyrrolo-[3,4-c]pyrroles of the formula

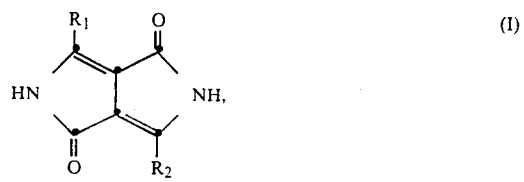

wherein each of $R_1$ and $R_2$ independently of the other is an isocyclic or heterocyclic aromatic radical, which process comprises reacting 1 mole of a disuccinate with 2 moles of a nitrile of the formula

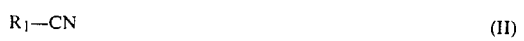

$$R_1-CN \qquad (II)$$

or

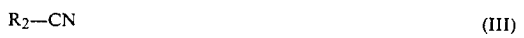

$$R_2-CN \qquad (III)$$

or with 1 mole of a nitrile of the formula (II) and 1 mole of the nitrile of the formula (III), in an organic solvent and in the presence of a strong base at elevated temperature, and obtaining the compound of formula I from the reaction product by hydrolysis.

The pyrrolo-[3,4-c]pyrroles are suitable for pigmenting organic material of high molecular weight.

10 Claims, No Drawings

PREPARATION OF PYRROLO[3,4-C]PYRROLES

The present invention relates to a process for the preparation of 1,4-diketopyrrolo[3,4-c]pyrroles which are valuable pigments. A process for the preparation of 1,4-diketo-3,6-diphenylpyrrolo[3,4-c]pyrrole starting from benzonitrile and ethyl bromoacetate in the presence of activated zinc-copper couple is described in Tetrahedron Lett. 1974, 2549-52. However, the yields obtained up to now have been unsatisfactory. By starting from a succinate and an aromatic nitrile, then under specific reaction conditions the desired pyrrolo[3,4-c]pyrrole pigments are obtained in substantially higher yield. Furthermore, the process of this invention affords novel pyrrolo[3,4-c]pyrroles which are not obtainable, or are obtainable only with very great difficulty, by the prior art process.

Accordingly, the present invention provides a process for the preparation of 1,4-diketopyrrolo[3,4-c]pyrroles of the formula

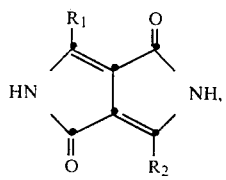

(I)

wherein each of $R_1$ and $R_2$ independently of the other is an isocyclic or heterocyclic aromatic radical, which process comprises reacting 1 mole of a disuccinate with 2 moles of a nitrile of the formula $$R_1-CN \quad (II)$$

or $$R_2-CN \quad (III)$$

or with 1 mole of a nitrile of the formula (II) and 1 mole of the nitrile of the formula (III), in an organic solvent and in the presence of a strong base at elevated temperature, and obtaining the compound of formula I from the reaction product by hydrolysis.

The radicals $R_1$ and $R_2$ may be different or identical, but are preferably identical. $R_1$ and $R_2$ as isocyclic aromatic radicals are preferably monocyclic to tetracyclic radicals, most preferably monocyclic or bicyclic radicals, i.e. phenyl, diphenylyl or naphthyl. Heterocyclic aromatic radicals $R_1$ and $R_2$ are preferably monocyclic to tricyclic radicals. These radicals may be entirely heterocyclic or may contain a heterocyclic ring and one or more fused benzene rings, and the cyano group can be linked both to the heterocyclic and to the isocyclic moiety respectively. Examples of heterocyclic aromatic radicals are: pyridyl, pyrimidyl, pyrazinyl, triazinyl, furyl, pyrrolyl, thiophenyl, quinolyl, cumarinyl, benzfuranyl, benzimidazolyl, benzoxazolyl, dibenzfuranyl, benzothiophenyl, dibenzothiophenyl, indolyl, carbazolyl, pyrazolyl, imidazolyl, oxazolyl, isoxazolyl, thiazolyl, indazolyl, benzthiazolyl, pyridazinyl, cinnolyl, quinazolyl, quinoxalyl, phthalazinyl, phthalazindionyl, phthalamidyl, chromonyl, naphtholactamyl, quinolonyl, ortho-sulfobenzimidyl, maleinimidyl, naphtharidinyl, benzimidazolonyl, benzoxazolonyl, benzthiazolonyl, benzthiazothionyl, quinazolonyl, quinoxalonyl, phthalazonyl, dioxopyrimidinyl, pyridonyl, isoquinolonyl, isoquinolinyl, isothiazolyl, benzisoxazolyl, benzisothiazolyl, indazolonyl, acridinyl, acridonyl, quinazolindionyl, quinoxalindionyl, benzoxazindionyl, benzoxazinonyl and naphthalimidyl. Both the isocyclic and the heterocyclic aromatic radicals may contain the customary non-watersolubilising substituents such as:

(1) Halogen atoms, e.g. chlorine, bromine or fluorine atoms.

(2) Branched or unbranched alkyl groups containing preferably 1 to 18, especially 1 to 12, more particularly 1 to 8 and, most preferably, 1 to 4, carbon atoms. These alkyl groups may contain non-watersolubilising substituents, e.g. fluorine, hydroxyl, cyano, $-OCOR_3$, $-OR_4$, $-COOR_3$, $-CONR_4R_5$ or $-R_3-OCONHR_3$, wherein $R_3$ is alkyl, aryl such as napthyl, or benzyl or benzyl substituted by halogen, alkyl or $-O-$alkyl, or is a heterocyclic radical; $R_4$ and $R_5$ are hydrogen, alkyl or alkyl substituted by cyano or hydroxy, or is $C_5-C_6$cycloalkyl, aryl or heteroaryl, especially phenyl or phenyl substituted by halogen, alkyl or $-O-$alkyl, or wherein $R_4$ and $R_5$ together with the nitrogen atom form a 5- or 6-membered heterocyclic ring, e.g. a morpholine, piperidine or phthalimide ring. Further possible substituents at the alkyl groups are mono- or dialkylated amino groups, aryl radicals such as naphthyl or preferably phenyl or phenyl substituted by halogen, alkyl or $-O-$alkyl, or also heterocyclic aromatic radicals such as 2-thienyl, 2-benzoxazolyl, 2-benzthiazolyl, 2-benzimidazolyl, 6-benzimidazolonyl, 2-, 3- or 4-pyridyl, or 2-, 4- or 6-quinolyl radicals.

If the substituents specified in (2) above in turn contain alkyl, then this alkyl may be branched or unbranched and contain preferably 1 to 18, especially 1 to 12, more particularly 1 to 8 and, most preferably, 1 to 4 carbon atoms.

Examples of unsubstituted or substituted alkyl groups are: methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluoroethyl, cyanomethyl, methoxycarbonylmethyl, acetoxymethyl or benzyl.

(3) The $-OR_6$ group, wherein $R_6$ is hydrogen, alkyl, or aryl such as naphthyl or preferably phenyl or phenyl substituted by halogen, alkyl or $-O-$alkyl, or is $C_5-C_6$cycloalkyl, aralkyl or a heterocyclic radical. In the definition of $R_6$, alkyl may contain a number of carbon atoms specified as preferred in (2) above. Typical examples of $R_6$ are: methyl, ethyl, n-propyl, isopropyl, trifluoroethyl, phenyl, o-, m- or p-chlorophenyl, o-, m- or p-methylphenyl, α- or β-naphthyl, cyclohexyl, benzyl, thienyl or pyranylmethyl.

(4) The $-SR_6$ group, wherein $R_6$ is as defined in (3) above. Typical examples of $R_6$ are: methyl, ethyl, n-propyl, isopropyl, phenyl, o-, m- or p-chlorophenyl, o-, m- or p-methylphenyl, α- or β-naphthyl, cyclohexyl, benzyl, thienyl or pyranylmethyl.

(5) The cyano group.

(6) The group of the formula $-NR_4R_5$, wherein $R_4$ and $R_5$ are as defined in (2). Typical examples are: amino, methylamino, dimethylamino, ethylamino, diethylamino, isopropylamino, β-hydroxyethylamino, β-hydroxypropylamino, N,N-bis-(β-hydroxyethyl)amino, N,N-bis-(β-cyanoethyl)amino, cyclohexylamino, phenylamino, N-methylphenylamino, benzylamino, dibenzylamino, piperidyl or morpholyl.

(7) The group of the formula —COOR$_3$, wherein R$_3$ is as defined in (2). Examples of R$_3$ are: methyl, ethyl, isopropyl, tert-butyl, n-butyl, phenyl, benzyl or furfuryl.

(8) The group of the formula —COR$_6$, wherein R$_6$ is as defined in (3). Examples of R$_6$ are: methyl, ethyl, tert-butyl, phenyl, o-, m- or p-chlorophenyl, o-, m- or p-methylphenyl or α- or β-naphthyl.

(9) The group of the formula —NR$_7$COR$_3$, wherein R$_3$ is as defined in (2). R$_7$ is hydrogen, alkyl, aryl, e.g. naphthyl or preferably phenyl or phenyl substituted by halogen, alkyl or —O—alkyl, or is C$_5$-C$_6$cycloalkyl, aralkyl or the radical —COR$_3$, whilst two radicals —COR$_3$ together with the nitrogen atom are able to form a heterocyclic ring. In the definition of R$_7$, alkyl may contain a number of carbon atoms specified as preferred in (2) above. Typical examples are: acetylamino, propionylamino, butyrylamino, benzoylamino, p-chlorobenzoylamino, p-methylbenzoylamino, N-methylacetylamine, N-methylbenzoylamino, N-succinimido or N-phthalimido.

(10) The group of the formula —NR$_6$COOR$_3$, wherein R$_3$ and R$_6$ are as defined in (2) and (3) respectively. Typical examples are the —NHCOOCH$_3$, NHCOOC$_2$H$_5$ or NHCOOC$_6$H$_5$ groups.

(11) The group of the formula —NR$_6$CONR$_4$R$_5$, wherein R$_6$, R$_5$, and R$_4$ are as defined in (3) and (2). Typical examples are: ureido, N-methylureido, N-phenylureido or N,N-2',4'-dimethylphenylureido.

(12) The group of the formula —NHSO$_2$R$_3$, wherein R$_3$ is as defined in (3). Typical examples are: methanesulfonylamino, phenylsulfonylamino, p-toluylsulfonylamino or β-naphthylsulfonylamino.

(13) The groups of the formula —SO$_2$R$_3$ or —SOR$_3$, wherein R$_3$ is as defined in (2) above. Typical examples are: methylsulfonyl, ethylsulfonyl, phenylsulfonyl, 2-naphthylsulfonyl, phenylsulfoxidyl.

(14) The group of the formula —SO$_2$OR$_3$, wherein R$_3$ is as defined in (2) above. Typical examples of R$_3$ are: methyl, ethyl, phenyl, o-, m- or p-chlorophenyl, o-, m- or p-methylphenyl, α- or β-naphthyl.

(15) The group of the formula —CONR$_4$R$_5$, wherein R$_4$ and R$_5$ are as defined in (2). Examples of R$_4$ and R$_5$ are: carbamoyl, N-methylcarbamoyl, N-ethylcarbamoyl, N-phenylcarbamoyl, N,N-dimethylcarbamoyl, N-methyl-N-phenylcarbamoyl, N-α-N-naphthylcarbamoyl or N-piperidylcarbamoyl.

(16) The group of the formula —SO$_2$NR$_4$R$_5$, wherein R$_4$ and R$_5$ are as defines in (2) above. Typical examples are: sulfamoyl, N-methylsulfamoyl, N-ethylsulfamoyl, N-phenylsulfamoyl, N-methyl-N-phenylsulfamoyl or N-morpholylsulfamoyl.

(17) The group of the formula —N=N—R$_8$, wherein R$_8$ is the radical of a coupling component or is a phenyl radical which is unsubstituted or substituted by halogen, alkyl or O—alkyl. In the definition of R$_8$, alkyl may contain a number of carbon atoms specified in (2) as preferred. Examples of R$_8$ are: acetoacetarylide, pyrazolyl, pyridonyl, o- or p-hydroxyphenyl, o-hydroxynaphthyl, p-aminophenyl or p-N,N-dimethylaminophenyl radicals.

(18) The group of the formula —OCOR$_3$, wherein R$_3$ is as defined in (2) above. Examples of R$_3$ are: methyl, ethyl, phenyl, o-, m- or p-chlorophenyl.

(19) The group of the formula —OCONHR$_3$, wherein R$_3$ is as defined in (2) above. Examples of R$_3$ are: methyl, ethyl, phenyl, o-, m- or p-chlorophenyl.

The preferred starting material employed in the preparation of compounds of the formula I according to this invention is a homogeneous nitrile of the formula II or III. It is also preferred to use nitriles of the formulae II and/or III, wherein R$_1$ and R$_2$ are unsubstituted phenyl or naphthyl or phenyl or naphthyl which contain non-watersolubilising substituents In particular, the starting materials employed are nitriles of the formula IV

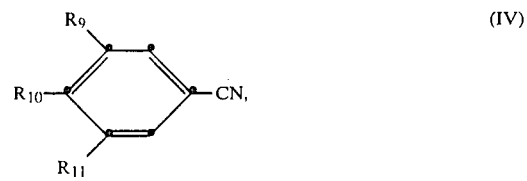

wherein each of R$_9$, R$_{10}$ and R$_{11}$ independently of one another is hydrogen, fluorine, chlorine, bromine, carbamoyl, cyano, trifluoromethyl, C$_2$-C$_{13}$alkylcarbamoyl, C$_1$-C$_{12}$alkyl, C$_1$-C$_{12}$alkoxy, C$_1$-C$_{12}$alkylmercapto, C$_2$-C$_{13}$alkoxycarbonyl, C$_2$-C$_{13}$alkanoylamino, C$_1$-C$_{12}$monoalkylamino, C$_2$-C$_{24}$dialkylamino or phenoxy, phenylmercapto, phenoxycarbonyl, phenylcarbamoyl or benzoylamino, each unsubstituted or substituted by halogen, C$_1$-C$_{12}$alkyl or C$_1$-C$_{12}$alkoxy, with the proviso that at least one of R$_9$, R$_{10}$ and R$_{11}$ is hydrogen.

Most preferably, the starting materials employed are nitriles of the formula V

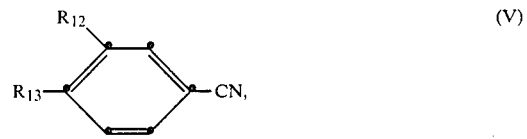

wherein one of R$_{12}$ and R$_{13}$ is chlorine, bromine, C$_1$-C$_4$alkyl, cyano, C$_1$-C$_4$alkoxy, or is phenoxy, carbamoyl or C$_2$-C$_5$alkylcarbamoyl, each unsubstituted or substituted by chlorine or methyl, or is phenylcarbamoyl which is unsubstituted or substituted by chlorine, methyl or methoxy, and the other is hydrogen.

The disuccinates to be used in the process of this invention may be dialkyl, diaryl or monoalkyl-monoaryl succinates. The dialkyl and diaryl succinates may also be unsymmetrical. However, it is preferred to use symmetrical disuccinates, most preferably symmetrical dialkyl succinates. If a diaryl or monoaryl-monoalkyl succinate is employed, aryl denotes preferably phenyl which is unsubstituted or substituted by halogen such as chlorine, C$_1$-C$_6$alkyl such as ethyl, methyl, isopropyl or tert-butyl, or C$_1$-C$_6$alkoxy such as methoxy or ethoxy. The preferred meaning of aryl is unsubstituted phenyl. If a dialkyl or monoalkyl-monoaryl succinate is employed, then alkyl may be unbranched or branched, preferably branched, and may contain preferably 1 to 18, in particular 1 to 12, more particularly 1 to 8 and most preferably 1 to 5, carbon atoms. Branched alkyl is preferably sec- or tert-alkyl, e.g. isopropyl, sec-butyl, tert-butyl, tert-amyl and cyclohexyl.

Examples of disuccinates are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl] succinate, di-[1,1,3,3- tetramethylbutyl] succinate, di-[1,1-dimethylpentyl] succinate, di-[1-methyl-1-ethylbutyl] succinate, di-[1,1-diethylpropyl] succinate, diphenyl succinate, di[4-methylphenyl] succinate, di-[2-methylphenyl] succinate, di-[4-chlorophenyl] succinate, monoethyl-monophenyl succinate, and dicyclohexyl succinate.

The disuccinates and the nitriles of the formula II or III are known compounds and may be prepared by known methods.

The reaction of the disuccinate with the nitrile is carried out in an organic solvent. Examples of suitable solvents are primary, secondary or tertiary alcohols containing 1 to 10 carbon atoms, e.g. methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, 2,4,4-trimethyl-2-pentanol, or glycols such as ethylene glycol or diethylene glycol; and also ethers such as tetrahydrofuran or dioxan, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene, N-methylpyrrolidone; aliphatic or aromatic hydrocarbons such as benzene or benzene substituted by alkyl, alkoxy or halogen, e.g. toluene, xylene, anisole or chlorobenzene; or aromatic heterocyclic compounds such as pyridine, picoline or quinoline. In addition, it is also possible to use the nitrile of the formula II or III simultaneously as solvent if it is liquid in the temperature range in which the reaction takes place. Mixtures of the above solvents may also be used. It is convenient to use 5 to 20 parts by weight of solvent per 1 part by weight of reactants.

In the process of this invention it is preferred to use an alcohol as solvent, in particular a secondary or tertiary alcohol. Preferred tertiary alcohols are tert-butanol and tert-amyl alcohol. Mixtures of these preferred solvents with aromatic hydrocarbons such as toluene or xylene, or halogen-substituted benzene such as chlorobenzene, are also of particular interest.

The process of the present invention is carried out in the presence of a strong base. Suitable strong bases are in particular the alkali metals themselves such as lithium, sodium or potassium, or alkali metal amides such lithium amide, sodium amide or potassium amide, or alkali metal hydrides such as lithium, sodium or potassium hydride, or alkaline earth metal alcoholates or alkali metal alcoholates which are derived preferably from primary, secondary or tertiary aliphatic alcohols containing 1 to 10 carbon atoms, e.g. lithium methylate, sodium methylate or potassium methylate, or lithium, sodium or potassium ethylate, lithium, sodium or potassium n-propylate, lithium, sodium or potassium isopropylate, lithium, sodium or potassium n-butylate, lithium, sodium or potassium sec-butylate, lithium, sodium or potassium tert-butylate, lithium, sodium or potassium 2-methyl-2-butylate, lithium, sodium or potassium 2-methyl-2-pentylate, lithium, sodium or potassium 3-methyl-2-pentylate, lithium, sodium or potassium 3-methyl-3-pentylate, lithium, sodium or potassium 3-ethyl-3-pentylate. However, a mixture of the above bases may also be employed.

In the process of this invention the preferred strong base is an alkali metal alcoholate, the alkali being preferably sodium or potassium and the alcoholate being preferably derived from a secondary or tertiary alcohol. Particularly preferred strong bases are therefore e.g. sodium or potassium isopropylate, sodium or potassium sec-butylate, sodium or potassium tert-butylate and sodium or potassium tert-amylate. Moreover, the alkali metal alcoholates may also be prepared in situ by reacting the appropriate alcohol with the alkali metal, alkali metal hydride or alkali metal amide.

In the process of this invention the strong base may be employed in an amount of preferably 0.1 to 10 moles, most preferably 1.9 to 4.0 moles, based on 1 mole of disuccinate. Although in principle stoichiometric amounts of base suffice, an excess of base often has an advantageous influence on the yield.

The process of the invention is preferably carried out in the temperature range from 60° to 140° C., with the preferred range being from 80° to 120° C.

The hydrolysis of the condensation product may be carried out with water, an alcohol containing 1 to 4 carbon atoms such as methanol or ethanol, but preferably with an acid. Examples of suitable acids are aliphatic or aromatic carboxylic or sulfonic acids, e.g. formic acid, acetic acid, propionic acid, oxalic acid, benzoic acid or benzenesulfonic acid. Further suitable acids are also mineral acids such as hydrochloric acid, sulfuric acid or phosphoric acid. It is preferred to use an organic acid for the hydrolysis, especially an aliphtic carboxylic acid such as acetic acid.

In the course of the hydrolysis the compound of formula I precipitates and can be isolated by filtration.

For the reaction of the disuccinate with the nitriles of the formulae II to V it is in principle possible to charge the reaction vessel, at low temperature, with all the components and then to heat the mixture to the range of the reaction temperature, or to add the individual components, in any order, to each other in the range of the reaction temperature. A preferred embodiment of the reaction, which usually has a particularly advantageous influence on the yield, consists in charging the reaction vessel with the nitrile and the base and then adding the disuccinate in the range of the reaction temperature. A further possibility consists in adding the disuccinate and the nitrile simultaneously to the base. It is entirely possible to carry out the process of the invention not only batchwise, but also continuously.

In particular, when using disuccinates containing alkyl radicals and alcoholates which are derived from lower alcohols such as methanol, ethanol, n-propanol, isopropanol or tert-butanol, it may be necessary to remove the lower alcohol formed during the reaction from the reaction medium continuously in order to obtain higher yields.

If an alcohol is used as solvent and an alcoholate as base, it may be advantageous to choose an alcohol and an alcoholate having the same alkyl moieties. It may likewise be advantageous if, in addition, the disuccinate also contains such alkyl groups.

A further preferred embodiment of the process consists in using the nitrile to be reacted with the disuccinate in more than only stoichiometric proportions. It has been found that the yield of final product can usually be further improved by using an excess of nitrile over the disuccinate, in which case the optimum amount must be determined according to the respective reactants and may be up to ten times the stoichiometric amount required with respect to the disuccinate. It is normally possible to recover excess nitrile. An excess of disuccinate over the nitrile can often have a positive influence on the yield, in which case the excess may be up to twice the stoichiometrically required amount of disuccinate.

The compounds of the formula I obtained by the process of this invention are novel if $R_1$ and $R_2$ are radicals of aromatic N-heterocyclic ring systems. These N-heterocyclic ring systems may be unsubstituted or substituted by halogen, cyano, carbamoyl, trifluoromethyl, or alkyl or alkoxy each containing preferably 1 to 18, in particular 1 to 8, and most preferably 1 to 4, carbon atoms. $R_1$ and $R_2$ may be e.g. radicals of pyrrole, indole, pyrazole, imidazole, benzimidazole, oxazole, isoxazole, benzoxazole, thiazole, isothiazole, benzisothiazole, indazole, pyridine, quinoline, isoquinoline, pyridazine, pyrazine, pyrimidine, 1,2,4- and 1,3,5-triazine, acridine, cinnoline, quinazoline, quinoxaline or naphtharidine. As radicals of aromatic N-heterocyclic ring systems, $R_1$ and $R_2$ are preferably quinolyl, isoquinolyl, but are most preferably o-, m- or p-pyridyl.

Depending on the nature of their substituents and on the polymers to be coloured, the compounds of formula I may also be used as polymer-soluble colourants. Normally, however, the compounds of formula I are used as pigments for organic materials of high molecular weight and can be used in general direct in the form in which they are obtained by the process of this invention.

Depending on the end use, the pigments obtained by the process of the invention can be converted into a more opaque or more transparent form. To obtain a transparent form, the hydrolysis is preferably carried out at lower temperature (below 80° C.)

If it is desired to obtain a more opaque pigment form, it is convenient to carry out a hydrolysis at more elevated temperature (above 80° C.), with or without pressure. It is also possible first to isolate the pigment after the hydrolysis and then to heat it in water or an organic solvent, with or without pressure, in order to obtain the opaque form. It is preferred to employ an organic solvent having a boiling point above 80° C. Particularly suitable solvents are benzenes which are substituted by halogen atoms or by alkyl or nitro groups, e.g. xylenes, chlorobenzene, o-dichlorobenzene or nitrobenzene, as well as pyridine bases such as pyridine, picoline or quinoline, and also ketones such as cyclohexanone, ethers such ethylene glycol monomethyl or monoethyl ether, amides such as dimethylformamide or N-methylpyrrolidone, and also dimethylsulfoxide or sulfolane. The aftertreatment may also be carried out in water in the presence of an organic solvent and/or with the addition of surface-active compounds.

Depending on the envisaged end-use, it may be advantageous to prepare mixtures of compounds of the formula I. This can be done for example by mixing different reaction solutions which have been prepared independently of one another before the hydrolysis, hydrolysing them together and then isolating the resultant mixture of compounds of the formula I. It is also possible to reprecipitate two or more compounds of the formula I together.

Organic materials of high molecular weight which may be pigmented with the compounds of formula are e.g. cellulose ethers and esters such as ethyl cellulose, nitrocellulose, cellulose acetate, cellulose butylate, natural resins or synthetic resins such as polymerisation resins or condensation resins, e.g. aminoplasts, in particular urea/formaldehyde and melamine/formaldehyde resins, alkyd resins, phenolic plastics, polycarbonates, polyolefins such as polystyrene, polyvinyl chloride, polyethylene, polypropylene, polyacrylonitrile, polyacrylates, polyamides, polyurethanes or polyesters, rubber, casein, silicone and silicone resins, individually or in mixtures.

It is immaterial whether the above organic compounds of high molecular weight are in the form of plastics, melts or of spinning solutions, lacquers, paints or painting inks. Depending on the end use, it is advantageous to use the pigments of this invention in the form of toners or formulations. The compounds of the formula I are employed in an amount of preferably 0.1 to 10% by weight, based on the organic material of high molecular weight to be pigmented.

The colorations obtained, e.g. in plastics, filaments, lacquers or printing inks, have excellent tinctorial strength, good dispersibility, good fastness to overspraying, migration, heat, light and atmospheric influences, as well as good gloss.

The invention is illustrated by the following examples.

EXAMPLE 1

A substantially anhydrous mixture of 48.2 ml of tert-amyl alcohol, 17.3 g of potassium tert-butylate and 72.2 g of benzonitrile is heated to about 98° C. under a nitrogen atmosphere. As soon as this temperature has been reached, a substantially anhydrous solution of 7.31 g of dimethyl succinate in 5 ml of tert-amyl alcohol is added over 145 minutes by means of a metering pump. The temperature is kept constantly at 98°-99° C. and methanol is distilled off. When the addition is complete, the reaction mixture is kept for 2 hours at 99° C., then cooled to 65° C., diluted slowly with 100 ml of methanol, slowly neutralised with 10.8 ml of glacial acetic acid and boiled briefly at reflux temperature. The resultant pigment suspension is filtered at about 50° C. The filter cake is suspended in 300 ml of methanol and the pigment is isolated again by filtration, then finally washed wih methanol and water until the washings run colourless, and dried at 80° C. in vacuo. affording 9.04 g (62.8% of theory, based on dimethyl succinate) of pure pigment of the formula VI

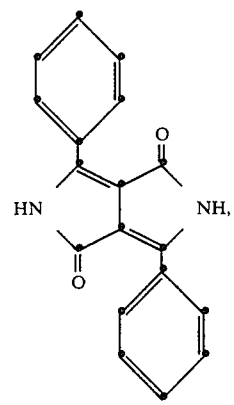

(VI)

which colours PVC red.

Instead of using dimethyl succinate, it is also possible to use diethyl succinate with no particular disadvantage.

EXAMPLE 2

23 g of potassium tert-butylate are suspended in 100 ml of anhydrous tert-amyl alcohol and substantially dissolved. Then 20.6 g of benzonitrile are added and the mixture is heated to about 97° C. As soon as this temperature has been reached, a solution of 23 g of di-tert-butyl succinate and 10 ml of tert-amyl alcohol is stirred in over 3¼ hours using a metering pump. The reaction temperature is kept at 96°–98° C. and tert-butyl alcohol is partially removed by distillation. When the addition is complete, the reaction mixture is kept for 2 hours at 95°–97° C. and then worked up as in Example 1, using 13.2 ml instead of 10.8 ml of glacial acetic acid. The filter cake is dried in vacuo at 80° C., affording 17.6 g of pure pigment of the formula VI (60.9% of theory, based on the ester employed). Unreacted benzonitrile can be recovered from the mother liquor.

EXAMPLE 3

4.6 g of sodium are first dissolved in 65 ml of sec-butyl alcohol at reflux temperature (about 97° C.) over about 5 hours. The solution is cooled to about 50° C., then 51.6 g of benzonitrile are added and the mixture is heated to 97° C. Then 23 g of di-sec-butyl succinate are added over about 3 hours using a metering pump, while keeping the reaction temperature constantly at 97° C. (reflux temperature). When the addition is complete, the mixture is kept for 1½ hours at 97° C. and then worked up as in Example 1, using 12.6 ml instead of 10.8 ml of glacial acetic acid. The filter cake is dried at 80° C. in vacuo, affording 8.7 g of pure pigment of the formula VI (30.2% of theory, based on the ester employed).

EXAMPLES 4–14

23 g of potassium tert-butylate are suspended in about 95 ml of anhydrous tert-amyl alcohol and substantially dissolved by stirring. Then 0.2 mole of the nitrile of the formula R—CN, wherein R has the meaning indicated in Table 1, is added. The mixture is heated to the temperature indicated in Table 1. As soon as this temperature has been reached, a solution consisting of 13.25 ml of dimethyl succinate and 5 ml of tert-amyl alcohol is added by means of a metering pump over the period of time indicated in Table 1 and with gentle stirring. The indicated temperature is maintained and methanol is distilled off. If the mixture becomes too viscous, it can be diluted with a small amount of tert-amyl alcohol. When the addition is complete, the reaction mixture is kept at the same temperature for 2 hours and worked up as in Example 1, using 13.2 ml instead of 10.8 ml of glacial acetic acid. The filter cake is then dried at 80° C. in vacuo to give the pigment of the formula

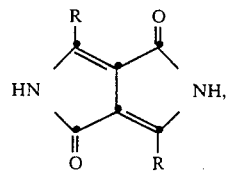

wherein R has the meaning given in Table 1, in the indicated yield.

TABLE 1

| Example | R | Reaction temperature in °C. | Addition time in hours | Yield in % of theory, based on di-succinate | Shade in PVC (0.2 %) |
|---|---|---|---|---|---|
| 4 | H₃C—⌬ | 97–99 | 3¾ | 23.4 | red |
| 5 | ⌬—Cl | 89–91 | 2 | 56.8 | orange |
| 6 | Cl—⌬ | 88–91 | 2 | 39.5 | claret |
| 7 | CH₃OOC—⌬ | 89–91 | 2¼ | 6.6 | red |
| 8 | ⌬—CN | 89–91 | 2¼ | 77.5 | reddish |
| 9 | NC—⌬ | 90–91 | 2¼ | 80.0 | claret |

TABLE 1-continued

| Example | R | Reaction temperature in °C. | Addition time in hours | Yield in % of theory, based on disuccinate | Shade in PVC (0.2 %) |
|---|---|---|---|---|---|
| 10 | (pyridyl) | 89–90 | 1¾ | 43.1 | red |
| 11 | (pyridyl) | 89–91 | 1¾ | 67.6 | red |
| 12 | (pyridyl) | 87–92 | 2 | 76.5 | red |
| 13 | (naphthyl) | 95–97 | 2 | 4.5 | orange |
| 14 | (methylnaphthyl) | 96–97 | 1¾ | 24.2 | red |

EXAMPLES 15-37

8.3 g of sodium and 0.12 g of sodium bis-2-acetylhexyl sulfosuccinate are added, under nitrogen, to 145 ml of tert-amyl alcohol. With gentle stirring, the mixture is heated to 95°–102° C. As soon as the sodium has melted, the emulsion is stirred vigorously for 3 to 5 hours at 95°–102° C. To the resultant solution is added 0.24 mole of the nitrile of the formula R'—CN or R"—CN, wherein R' and R" are identical and are as defined in Table II (Examples 15 to 25), or 0.12 mole of the nitrile of the formula R'—CN and 0.12 mole of the formula R"—CN, wherein R' and R" are different and are as defined in Table II (Examples 26-37). By means of a metering pump, 1.2 moles of diisopropyl succinate dissolved in 12 ml of tert-amyl alcohol are added at the reaction temperature indicated in Table II over the period of time also indicated therein, while continuously distilling off isopropanol. When the addition is complete, the mixture is kept for 2 hours at the reaction temperature and then worked up as in Example 1. The filter cake is dried at 80° C. in vacuo to give the pigment of the formula $$\text{R'} \underset{HN}{\overset{O}{\diagup\!\!\!\diagdown}} \underset{NH}{\overset{O}{\diagdown\!\!\!\diagup}} \text{R"}$$

wherein R' and R" are defined in Tables II and III, in the yield also indicated in the tables.

TABLE II

| Example | R'=R" | Reaction temperature in °C. | Addition time in hours | Yield in % of theory, based on disuccinate | Shade in PVC (0.2%) |
|---|---|---|---|---|---|
| 15 | F₃C— 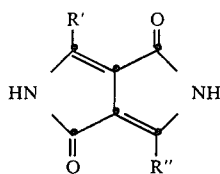 | 105–110 | 3 | 56.8 | orange-yellow |

TABLE II-continued

| Example | R'=R" | Reaction temperature in °C. | Addition time in hours | Yield in % of theory, based on disuccinate | Shade in PVC (0.2%) |
|---|---|---|---|---|---|
| 16 | CH₃(CH₂)₄O—pyridyl | 105–110 | 3 | 65.0 | red |
| 17 | F₃C—phenyl | 105–110 | 2.5 | 44.9 | red |
| 18 | NC—biphenyl | 105–110 | 3 | 36.7 | reddish violet |
| 19 | biphenyl | 105–110 | 2.5 | 10.0 | claret |
| 20 | (CH₃)₃C—phenyl | 105–110 | 2 | 55.2 | red |
| 21 | 3,4-dimethylphenyl | 105–110 | 2 | 52.4 | red |
| 22 | furyl (O) | 90 | 1 | 17.9 | violet |
| 23 | H₃C—phenyl (para) | 105–110 | 2 | 41.8 | red |
| 24 | thienyl (S) | 85 | 1 | 42.0 | claret |
| 25 | 3,4-dichlorophenyl | 85 | 1 | 70.4 | red |

TABLE III

| Example | R' | R" | Reaction temperature in °C. | Addition time in hours | Yield in % of theory, based on disuccinate | Shade in PVC (0.2%) |
|---|---|---|---|---|---|---|
| 26 | phenyl | 4-chlorophenyl | 105–110 | 2.5 | 66.9 | red |

TABLE III-continued

| Example | R' | R'' | Reaction temperature in °C. | Addition time in hours | Yield in % of theory, based on disuccinate | Shade in PVC (0.2%) |
|---|---|---|---|---|---|---|
| 27 |  |  | 90 | 1.3 | 64.1 | reddish violet |
| 28 |  | 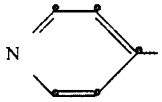 | 105–110 | 2.5 | 52.2 | red |
| 29 |  | 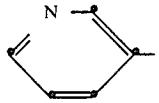 | 105–110 | 2.5 | 49.5 | orange |
| 30 | 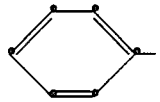 | 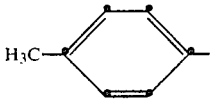 | 105–110 | 2.5 | 54.6 | red |
| 31 | 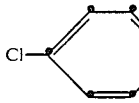 |  | 105–110 | 2.5 | 71.4 | red |
| 32 |  | 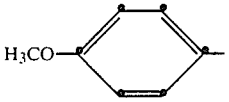 | 105–110 | 1 | 47.8 | red |
| 33 | 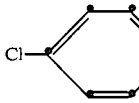 | 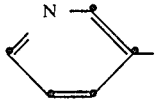 | 105–110 | 2.5 | 44.5 | red |
| 34 | 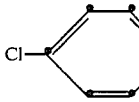 | 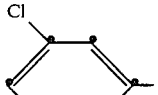 | 104 | 2.5 | 68.3 | orange |
| 35 | 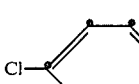 | 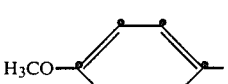 | 105–110 | 2.5 | 56.1 | claret |
| 36 | 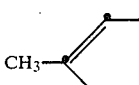 | 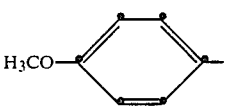 | 105–110 | 2.5 | 46.3 | red |
| 37 | 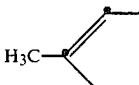 | 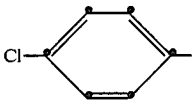 | 105–110 | 2.5 | 56.4 | claret |

EXAMPLE 38

4.6 g of sodium and 0.1 g of sodium lauryl sulfate as emulsifier are stirred vigorously in 117 ml of tert-amyl alcohol at 94°–100° C. until the sodium is completely dissolved. After the solution has cooled, 25.6 g of anhydrous isophthalodinitrile are added and a solution of 13.25 ml of dimethyl succinate and 5 ml of tert-amyl alcohol are added by means of a metering pump in the temperature range from 88°–92° C. over 2 hours. With stirring, the temperature is kept at 88°–92° C. and methanol is continuously distilled off. When the addition is complete, the reaction mixture is kept for 2 hours at 90° C. and then worked up as in Example 1, using 13.2 ml instead of 10.8 ml of glacial acetic acid. The filter cake is dried at 80° C. in vacuo, affording 25.5 g (75.5% of theory, based on dimethyl succinate) of the pigment of the formula

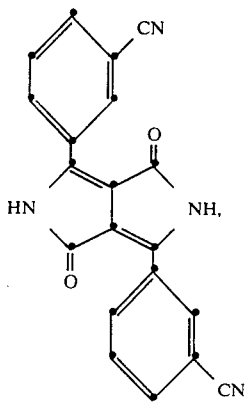

(VII)

which colours PVC in a reddish orange shade.

EXAMPLE 39

The procedure of Example 38 is repeated, using throughout sec-butyl alcohol instead of tert-amyl alcohol. Yield: 20.6 g (60.8% of theory, based on the ester) of the pigment of the formula VII.

EXAMPLE 40

The procedure of Example 38 is repeated, using tert-amyl alcohol as solvent and sodium tert-butylate prepared in situ as alcoholate. Yield: 22.9 g (67.8% of theory, based on the ester) of the pigment of the formula VII.

EXAMPLE 41

The reaction vessel is charged with 11.5 g of potassium tert-butylate in 17.4 ml of tert-amyl alcohol and 102.6 ml of benzonitrile. The mixture is heated to 100° C. and to it is added, at this temperature, a solution of 11.6 g of di-tert-butyl succinate in 5 ml of tert-amyl alcohol over 3 hours (addition by means of a metering pump). After 2 hours at 100° C., the reaction mixture is worked up as in Example 1, using 7.2 ml instead of 10.8 ml of glacial acetic acid. The filter cake is dried at 80° C. in vacuo, affording 10.15 g (70.4% of theory, based on the ester) of pure pigment of the formula VI.

EXAMPLE 42

11.5 g of potassium tert-butylate are suspended in 53.2 ml of tert-amyl alcohol and to this suspension are added 36.8 ml of benzonitrile. The mixture is heated to 98° C. and to it is added, at this temperature, a solution of 13.6 g of diphenyl succinate in 35 ml of benzonitrile over 2¾ hours. After 1½ hours at 100° C., the reaction mixture is worked up as in Example 1, using 6.9 ml instead of 10.8 ml of glacial acetic acid. The filter cake is dried at 80° C. in vacuo, affording 1.66 g (11.5% of theory), based on the ester) of the pigment of the formula VI.

EXAMPLE 43

11.5 g of potassium tert-butylate are suspended in 100 ml of toluene and the mixture is heated to 90° C. Then a solution of 6.63 ml of dimethyl succinate and 25.6 ml of benzonitrile is added over 2 hours. The reaction mixture is stirred for 16 hours at 90° C. and then worked up as in Example 1, using 7.2 ml instead of 10.8 ml of glacial acetic acid. The filter cake is dried in vacuo, affording 2.54 g (17.6% of theory, based on the ester) of the pigment of the formula VI.

EXAMPLE 44

The reaction vessel is charged with 4.6 g of sodium and 0.1 g of sodium lauryl sulfate in 70 ml of tert-amyl alcohol. This suspension is heated to reflux temperature (95°–100° C.) and then 20.7 ml of tert-butyl alcohol are added dropwise over 2 hours. The mixture is kept at reflux temperature (95°–100° C.) until the metal is completely dissolved. After the solution has cooled to room temperature, 59.2 g of 4-tolunitrile are added and the mixture is heated to 97° C. Then a solution of 22.1 g of monoisopropyl-mono-tert-butyl succinate in 10 ml of tert-amyl alcohol is added over about 4 hours, while keeping the temperature constantly at 97°–99° C. The mixture is then stirred for 1½ hours at the same temperature and worked up as in Example 1, using 13.2 ml instead of 10.8 ml of glacial acetic acid. The filter cake is dried at 80° C. in vacuo, affording 15.4 g (48.6% of theory, based on the ester) of the pigment of the formula VIII

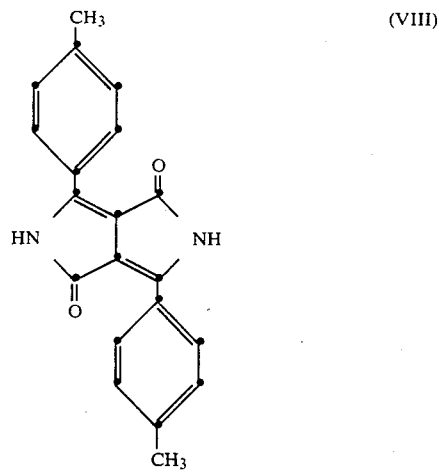

(VIII)

which colours PVC red.

EXAMPLE 45

4.6 g of potassium tert-butylate are suspended in 20 ml of 3-methyl-3-pentanol and to this suspension are added 5.94 g of 4-dimethylaminobenzonitrile. The mixture is heated to 120° C. and then a solution of 2.65 ml of dimethyl succinate in 6 ml of 3-methyl-3-pentanol are added dropwise over 2 hours. After 2 hours at 120° C., the reaction mixture is worked up as in Example 1, using 2.3 ml instead of 10.8 ml of glacial acetic acid. The filter cake is dried at 80° C. in vacuo, affording 0.28 g (3.7% of theory, based on the ester) of the pigment of the formula IX

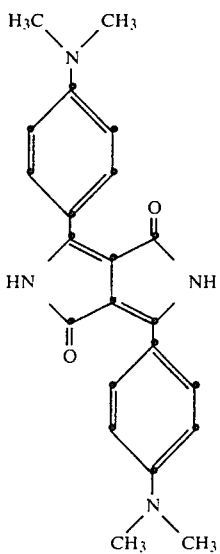

which colours PVC blue.

EXAMPLE 46

23 g of potassium tert-butylate are suspended in 145 ml of anhydrous tert-amyl alcohol and substantially dissolved by stirring. Then 12.8 g of terephthalonitrile and 12.8 g of isophthalonitrile are added. The mixture is heated to about 90° C. and then a solution of 13.25 ml of dimethyl succinate and 5 ml of tert-amyl alcohol are added over 2½ hours by means of a metering pump. The temperature is kept at about 90° C. and methanol is distilled off. When the addition is complete, the reaction mixture is kept for 1½ hours at about 90° C. and worked up as in Example 1, using 12.6 ml instead of 10.9 ml of glacial acetic acid. The filter cake is dried in vacuo at 80° C., affording 24.5 g (72.5% of theory, based on the ester) of the pigment of the formula X

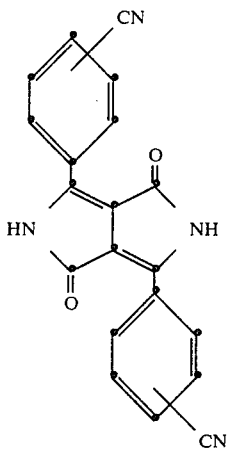

which colours PVC red.

EXAMPLE 47

7.43 ml of a 30% by weight solution of sodium methylate in methanol are added to 3.4 g of the pigment of Example 9 and 2.9 g of the pigment of Example 12 in 100 ml of anhydrous dimethylformamide. After stirring for about ¾ hour at room temperature, a solution of 2.52 ml of glacial acetic acid in 60 ml of methanol are added dropwise over 30 minutes and the suspension is stirred for several hours at room temperature. The suspension is filtered and the filter cake is washed and dried, affording 5.4 g of a mixture of the pigments of Examples 9 and 12.

EXAMPLE 48

To 1440 ml of anhydrous tert-amyl alcohol are added, under nitrogen, 82.8 g of sodium and 1.2 g of anhydrous sodium bis-2-ethylhexyl sulfosuccinate as emulsifier. The mixture is heated to about 100° C. and kept at reflux temperature until the metal is completely dissolved. The solution is cooled to about 80° C. and to it are then added 247.2 g of anhydrous benzonitrile. The mixture is then heated to about 110° C. and 242.4 g of anhydrous diisopropyl succinate are added over about 6 hours while simultaneously distilling off isopropanol. When the addition is complete, the reaction is allowed to go to completion over 2 hours and the reaction mixture is cooled to about 60° C. and diluted with 1650 ml of methanol. Then a mixture of 227 ml of glacial acetic acid and 150 ml of methanol is slowly added, whereupon the pigment precipitates. The precipitate is isolated by filtration at about 60° C. and washed in succession with 3000 ml of methanol and 2000 ml of hot water. The filter cake is dried at 70° C. in vacuo, affording 228.3 g (66% of theory, based on benzonitrile) of the pigment of the formula VI.

EXAMPLE 49

The procedure of Example 48 is repeated, using instead of diisopropyl succinate
(a) di-neopentyl succinate,
(b) di-2-butyl succinate,
(c) dicyclohexyl succinate or
(d) di-tert-butyl succinate,
to give the pigment of the formula VI in the following yields (% of theory, based on benzonitrile):
with ester (a): 64.9%
with ester (b): 65.2%
with ester (c): 71.5%
with ester (d): 75.7%.

EXAMPLE 50

The procedure of Example 48 is repeated, but the amounts of sodium and diisopropyl succinate are both increased by 30% by weight. The pigment of the formula VI is obtained in a yield of 81.9% of theory, based on benzonitrile.

EXAMPLE 51

The reaction vessel is charged, under argon, with 6.9 g of sodium in 100 ml of toluene and 26.5 g of 2-methyl-2-butanol. The mixture is stirred at reflux temperature (about 100° C.) until the metal is completely dissolved. A mixture of 21 ml of benzonitrile, 23 g of di-tert-butyl succinate and 20 ml of toluene is added dropwise at 70°–80° C. over 4 to 5 hours. The suspension is then stirred for about 19 hours at 80°–90° C., then neutralised at 60° C. by the dropwise addition of a mixture of 21 ml of glacial acetic acid and 80 ml of methanol over about 1½ hours, and stirred for another 30 minutes. The pigment suspension is filtered at 60° C. and the filter cake is washed first with methanol and then with water until the washings run colourless, then dried in a vacuum cabinet at 80° C. Yield: 23.8 g of pure pigment (≙82.5% of theory, based on di-tert-butyl succinate) of Example 1 of the formula VI.

EXAMPLE 52

The reaction vessel is charged, under argon, with 3.4 g of a 45% by weight dispersion of sodium is paraffin in 30 ml of toluene. A mixture of 14 ml of benzonitrile, 7.6 g of di-tert-butyl succinate and 27 ml of toluene is then added dropwise over about 2 hours. The temperature is raised gradually from 20° C. to 70° C. and the mixture is then stirred for about 20 hours at 80° C., whereupon the pigment precipitates. The suspension is neutralised with a mixture of 3.6 ml of glacial acetic acid and 27 ml of methanol and filtered. The filter cake is washed with acetone and then with water until the washings run colourless, then dried in a vacuum cabinet at 80° C. Yield: 5.6 g (=58.9% of theory, based on di-tert-butyl succinate) of the pigment of the formula VI.

EXAMPLE 53

The procedure of Example 48 is repeated, except that the mixture is neutralised with 8% by weight hydrochloric acid instead of with glacial acetic acid/methanol. After drying, a yield of 230 g (=66.5% of theory, based on diisopropyl succinate, of pure pigment of the formula VI is obtained.

What is claimed is:

1. A process for the preparation of a 1,4-diketopyrrolo[3,4-c]pyrrole of formula I

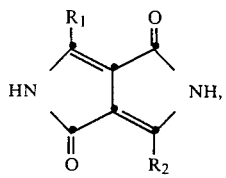

wherein
each of $R_1$ and $R_2$ independently of the other is phenyl or said phenyl substituted by one or two fluorine, chlorine or bromine atoms or mixtures thereof, by one, two or three methoxy or methyl groups or mixtures thereof with chlorine atoms, by cyano, by dimethylamino, by trifluoromethyl, by alkoxycarbonyl of 2 to 3 carbon atoms, by tert-butyl, by cyanophenyl, by acetyl or by alkylbenzoyloxy of 11-14 carbon atoms; biphenylyl; naphthyl or said naphthyl substituted by methoxy anthryl; phenanthryl; pyridyl or said pyridyl substituted by methyl or by amyloxy; quinolyl; furyl or thienyl, which consists essentially of
condensing an unsymmetrical or symmetrical dialkyl or diaryl succinate, or monoalkyl monoaryl succinate or dicyclohexyl succinate with two moles of nitrile per each mole of succinate, wherein the nitrile is of formula II or of formula III $$R_1CN \quad (II)$$

or $$R_2CN \quad (III)$$

or is an equimolar mixture of nitriles of formulas II and III; in an organic solvent which is an alkanol, a glycol, an ether, a glycol ether, a dipolar aprotic solvent, an aliphatic hydrocarbon, an aromatic hydrocarbon, benzene substituted by alkoxy or by halogen, pyridine, picoline or quinoline, or a mixture thereof; in the presence of 0.1 to 10 moles of a strong base per each mole of succinate, wherein said base is an alkali metal, an alkali metal amide, an alkali metal hydride, an alkali metal alcoholate or an alkaline earth metal alcoholate; at a temperature of 60° to 140° C., and
hydrolyzing the condensation reaction product obtained in water, a lower alkanol, a mineral acid or an organic acid or mixture thereof to form the compound of formula I.

2. A process according to claim 1, wherein the nitrile is a single nitrile of the formula II or III.

3. A process according to claim 1, wherein the disuccinate is a symmetrical dialkyl succinate containing 1 to 18 carbon atoms in each alkyl moiety.

4. A process according to claim 1, wherein the disuccinate is a symmetrical dialkyl succinate, wherein alkyl is sec- or tert-alkyl.

5. A process according to claim 1, wherein the solvent is a secondary or tertiary alcohol.

6. A process according to claim 1, wherein an organic acid is used for the hydrolysis.

7. A process according to claim 1 wherein each of $R_1$ and $R_2$ independently of the other is phenyl or said phenyl substituted by one or two chlorine atoms, by one or two methyl groups, by methoxy, by trifluoromethyl, by cyano, by methoxycarbonyl, by tert-butyl, by dimethylamino or by cyanophenyl; naphthyl; biphenylyl; pyridyl or said pyridyl substituted by amyloxy; furyl or thienyl.

8. A process according to claim 7 wherein each of $R_1$ and $R_2$ independently of the other is phenyl, 3-chlorophenyl, 4-chlorophenyl, 3,5-dichlorophenyl, 4-methylphenyl, 4-methoxyphenyl, 3-trifluoromethylphenyl, 4-trifluoromethylphenyl, 3-cyanophenyl, 4-cyanophenyl, 4-methoxycarbonylphenyl, 4-tert-butylphenyl, 4-dimethylaminophenyl, 4-(p-cyanophenyl)-phenyl, 1-naphthyl, 2-naphthyl, 4-biphenylyl, 2-pyridyl, 3-pyridyl, 4-pyridyl, 6-amyloxy-3-pyridyl, 2-furyl or 2-thienyl.

9. A process according to claim 1, wherein the strong base is an alkali metal alcoholate.

10. A process according to claim 9, wherein the alkali metal alcoholate is derived from a secondary or tertiary alcohol.

* * * * *